United States Patent [19]

Arnold et al.

[11] 4,016,300

[45] Apr. 5, 1977

[54] METHOD OF HEATING MICROBIAL CELLS

[75] Inventors: Philip M. Arnold; Emil A. Malick, both of Bartlesville, Okla.

[73] Assignee: Phillips Petroleum Company, Bartlesville, Okla.

[22] Filed: Dec. 4, 1975

[21] Appl. No.: 637,510

[52] U.S. Cl. .............................. 426/429; 426/60; 426/465; 426/656; 260/112 R

[51] Int. Cl.² ...................... A23J 3/00; A23J 1/18

[58] Field of Search .............. 426/60, 61, 62, 425, 426/429, 465, 471, 656, 665; 195/3 H, 28 R, 82, 96; 260/112 R; 203/14, 68, 70

[56] References Cited

UNITED STATES PATENTS

| | | | |
|---|---|---|---|
| 2,619,425 | 11/1952 | Levin | 203/14 X |
| 3,268,419 | 8/1966 | Champagnat et al. | 195/82 |
| 3,530,039 | 9/1970 | Bernheimer et al. | 195/96 |
| 3,720,585 | 3/1973 | Tannenbaum et al. | 195/98 |
| 3,782,967 | 1/1974 | Eriksen et al. | 426/62 |
| 3,891,772 | 6/1975 | Ridgway et al. | 426/60 |
| 3,904,485 | 9/1975 | du Chaffaut et al. | 195/28 R X |

*Primary Examiner*—Lionel M. Shapiro

[57] ABSTRACT

A method for heating microbial cells includes contacting of the cells, which are in a suitable medium forming a dispersion therewith, with heated $C_3$–$C_8$ hydrocarbons at preselected conditions of time, temperature and pressure sufficient for removal of the water. The dewatered cells are then suitably separated from the hydrocarbon heating medium whereby the cells are available for their intended use.

8 Claims, 1 Drawing Figure

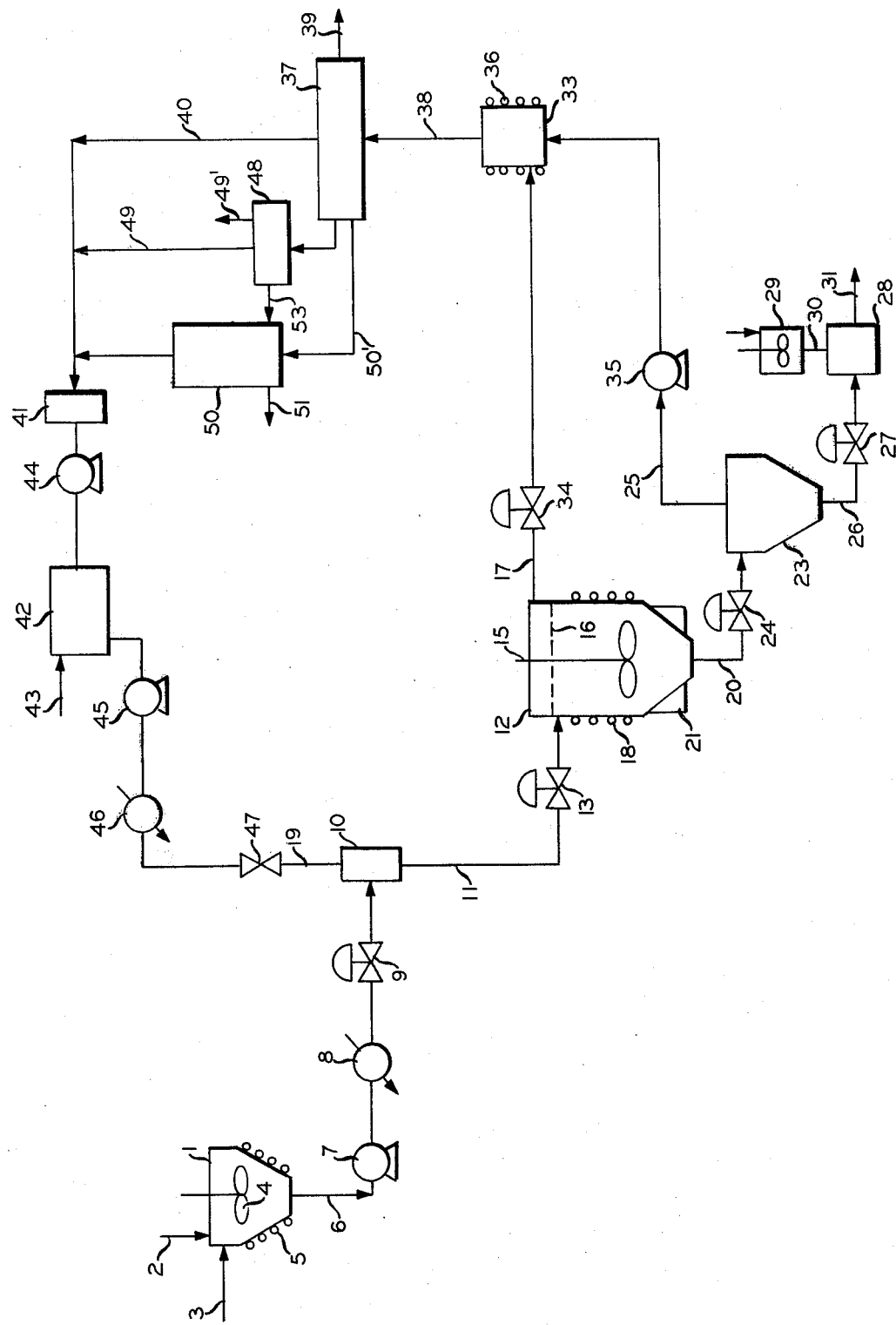

METHOD OF HEATING MICROBIAL CELLS

Current and projected world-wide food shortages have led to the development of processes for producing single cell protein by the culturing of microorganisms on various carbonaceous substrates to produce single cell protein which is edible by animals and/or humans. Many processes are known in the art for the production of single cell protein and same look promising for providing a relatively inexpensive source of single cell protein. The resulting product of these processes is usually a dispersion of microbial cells in an aqueous medium from which it is desirable to separate the microbial cells from the water and reduce the moisture content of the cells so same can be used as a food product.

Several processes are known for this separation but have posed certain problems in their practice. For example, one process uses heated edible cooking oils or fats for dewatering and cooking of yeast cells but such a process results in excessive residual oil or fat in the microbial cells which must then be removed by a secondary process such as solvent extraction. Such a process also has the problem of not being able to recycle all of the recovered cooking medium which therefore results in waste and extra expense in the overall process.

The principal objects and advantages of the present invention are: to provide a method and apparatus for the heating of a mixture of microbial cells and water to separate the water therefrom; to provide such a method which is efficient in operation and effectively separates water from the microbial cells; to provide such a method in which the cooking medium can be recovered and recycled with a minimum of degradation and loss of the cooking medium; to provide such a method which can also be used to improve nutritivity and taste of the resulting produced protein and which allows control of the physical condition of the produced protein; and, to provide such an apparatus and method which is well adapted for its intended use.

Other objects and advantages of the present invention will become apparent from the following detailed description taken in connection with the accompanying drawing wherein is set forth by way of illustration and example certain embodiments of the present invention.

FIG. 1 is a diagrammatic flow diagram of an apparatus used for the separation of water from microbial cells.

Referring more in detail to the drawing:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting but merely as a basis for the claims and as a representative basis for teaching one skilled in the art to variously employ the present invention in virtually any appropriate detailed manner.

In the practice of the present invention, microbial cells, as produced in a fermentation process by the cultivation of a microorganisms such as yeasts, bacteria or fungi, are taken from the fermentation apparatus and are a dispersion in an aqueous medium forming a mixture therewith. It is desired to dewater the mixture and dewater or separate the water from the microbial cells so that same are in a condition for use. The microbial cells contain protein and as such it is desirable to have a low moisture content as, for example, below 13 percent by weight of dry matter and more preferably, below 6 percent of weight of dry matter. (The water content referred to in the present claims and specification are values calculated on the basis of weight loss of the product after heating for 20 hours at 115° C at atmospheric pressure.) To accomplish the dewatering of the microbial cells, the mixture is contacted with a heating medium under the proper conditions of temperature, pressure and time to vaporize the water to thereby separate same from the microbial cells.

The heating medium is a hydrocarbon chosen from a group comprising $C_3-C_8$ hydrocarbons and preferably is an alkane chosen from the group comprising $C_3-C_8$ alkanes and most preferably is hexane. The medium can also be a mixture of two or more of the $C_3-C_8$ hydrocarbons. The contacting of the mixture and the heating medium is accomplished in an apparatus described below and the heating medium can be either in a gaseous condition or a liquid condition which is determined by the particular temperature and pressure combination used for the operating parameters. Because of the wide variety of microorganisms used to produce single cell protein, the particular operating conditions, i.e., temperature, pressure, time, and state of the heating medium, will be determined by the microorganism and also by the desired end product. End product variations which can be controlled by the instant invention include, for example, the moisture content and the degree of cell wall rupturing. It has been found that in certain cases it is desirable to rupture the cell wall whereby the protein is more readily assimilable by a consuming animal whereby more protein is assimilated rather than passed through the digestive system. This, of course, would be dependent upon the particular animal consuming the single cell protein.

The maximum temperature of the heating medium is below the degradation temperature of the single cell protein and the minimum temperature is determined by the operating pressure which in turn determines the minimum volatilization temperature of the water for a reasonable processing time. The choice of heating mediums will be determined by the particular processing parameters used in conducting the dewatering and the particular microbial cell being treated. It is known that the use of various hydrocarbons also effects removal of certain fats and lipids from the microbial cells which are objectionable in that they detract from the taste and odor of the single cell protein and it is desirable to remove same in certain instances.

Residence time of the microbial cells in an apparatus used for conducting the dewatering process is determined by the particular microorganism and the temperature and pressure at which the apparatus is being operated. The residence time can vary from a fraction of a second to several minutes.

After the dewatering, a mixture of microbial cells and heating medium is then separated in any suitable manner for removal of the heating medium from the microbial cells which are then ready for use for their intended purpose.

The heating medium is chosen on the basis of the particular processing parameters to be used, the microorganism to be processed and is also preferably immiscible in water and preferably has an azeotropic effect which allows the creation of a vapor phase in the cooking apparatus wherein the vapor created in the apparatus will contain the vaporized water and a certain amount of heating medium. Also, the heating medium which is selected preferably will not form hydrates or otherwise react at the operating conditions employed with constituents of the feed which contains the aqueous mixture of microbial cells and other constituents. Also, the heating medium preferably would not undergo any compositional or structural change or degradation and would be capable of efficient recovery for reuse in the process. Also, same would preferably not introduce any foreign taste or odor and would not pose any toxicological, pathogenic or carcinogenic characteristics to the single cell protein. The operating temperature of the process is from 100° to 250° C and more preferably 150° to 210° C, and most preferably 150° to 175° C, with the proper temperature being selected on the basis discussed above. The operating pressure can, for example, be as high as 10 atmospheres or higher, if desired.

FIG. 1 illustrates schematically an apparatus for conducting the present process. Feed which contains an aqueous mixture containing microbial cells and other fermentation constituents is introduced into a vessel 1 via a conduit 2 and, if desired, other components such as water, sterilizing agents, emulsifiers, flavor, color or other additives can be introduced into the vessel 1 via a conduit 3. A mixing device 4 can be provided in the vessel 1 to assure uniformity of mix. Also, a heat exchanger 5 can be provided to be in heat exchange relation with the vessel 1 for control of the temperature therein. An outlet conduit 6 communicates with the vessel 1 and preferably a pump 7 is connected in the conduit 6 to effect removal of the contents from the vessel 1. As shown, the conduit 6 can be provided with a heat exchanger 8 to control the temperature of the fluid flowing therethrough which passes through a flow regulator 9 to an optional mixing vessel 10. A conduit 11 connects the vessel 10 to a reactor 12 and, if desired, a flow and pressure regulator 13 can be provided in the conduit 11. As shown, the reactor 12 is provided with a mixing device 15. A baffle 16 is provided in the illustrated structure to prevent liquid and solids contained in the mixture in the reactor 12 from passing out with the overhead gases which are exhausted from the reactor 12 through a conduit 17 which communicates with an upper portion of the reactor 12. Also, a heat exchanger 18 can be provided to be in heat exchange relation with the reactor 12 for control of the temperature therein. The heating medium is introduced into the reactor 12 via the conduit 11 with the hydrocarbon being introduced into the mixing vessel 10 via a conduit 19. During operation of the reactor 12, overhead products are exhausted through the conduit 17 with the overhead products containing vaporized water and vaporized heating medium and the microbial cells collect in the lower portion of the reactor 12 and are discharged through a conduit 20 onto other processing equipment. If desired, a vibrator 21 can be provided to help induce flow of the microbial cells downwardly in the reactor 12 and out the discharge 20. The vibrator is particularly desirable because some microbial cells form a very cohesive mass and do not flow well under the influence of gravity.

The conduit 20 also communicates with a separating device 23 and it is to be noted that a pressure regulating valve 24 can be provided in the conduit 20 to control the discharge of product from the reactor 12 to the separating device 23. The function of the separating device 23 is to separate the microbial cells from the heating medium whereby the heating medium is discharged through a conduit 25 and the microbial cells are discharged through a conduit 26. The separating device 23 can be of a type which will vaporize the heating medium and/or provide centrifugal separation of the microbial cells from the heating medium. A valve 27 can be connected in the conduit 26 to control the discharge of microbial cells from the separating device 23 to a mixer 28 wherein the microbial cells can be mixed with other food ingredients, additives, coloring agents, etc., which are introduced thereinto from storage and mixing means 29 via a conduit 30. The microbial cells are then discharged from the mixer 28 via a discharge conduit 31 and are ready for use.

The heating medium discharged through the conduit 25 and the heating medium and water vapor discharged from the reactor 12 via the conduit 17 are introduced into a condenser 33. It is to be noted that the conduit 17 can have a pressure regulator 34 therein and the line 25 can be provided with a pump 35 to induce the flow of the heating medium into the condenser 33. The condenser 33 can be of any suitable type and, as shown, is provided with a heat exchanger 36 to maintain the proper operating temperature thereof. The condensed product from the condenser 33 is fed into a settling tank and/or separator-coalescer 37 via a conduit 38 communicating between same and the condenser 33. Separated water in the separator 37 is discharged through a conduit 39 out of the system. A conduit 40 connects the separator 37 to the conduit 19 and preferably a dryer 41 is connected in the conduit 40 for removing traces of water. The conduit 40, as shown, is connected to a reservoir 42 which is also connected to the conduit 19 providing communication therebetween for the recovered heating medium to be introduced back into the line 19 for reuse in the process. Fresh hydrocarbon can also be introduced into the reservoir 42 via a conduit 43 to make up for lost heating medium. As shown, a pump 44 is provided between the dryer 41 and the reservoir 42 to help effect the flow of recovered hydrocarbon therebetween.

As shown, a pump 45 is connected in the conduit 19 for inducing flow of hydrocarbon from the reservoir 42 to the mixing vessel 10. Also, a heat exchanger 46 can also be provided in the conduit 19 for heating of the hydrocarbon before same enters the reactor 12. A flow regulator 47 can also be provided in the line 19 for controlling the flow of hydrocarbon from the reservoir 42 to the reactor 12.

If desired, although not necessary, in certain processes if the feed flowing through conduit 6 contains components that remain dissolved in the cooking medium, the medium from the separator 37 can be passed through suitable separating means 48 such as a steam stripper which is connected between the dryer 41 and the separator 37 by a conduit 49 to effect removal of the undesirable components which can be discharged therefrom via outlet 49'. Further, if desired, if sufficient water is not removed by the separating means 37 a secondary water separating means 50 can be provided between the separator 37 and the dryer 41 connected thereto by a conduit 50'. The separating means 50 can be of conventional type with the water separated being discharged through a conduit 51. Also, if desired, a conduit 53 can be provided to communicate between the separating means 48 and 50 whereby excess water which would be in the separating means 48 can be removed by the separating means 50 before the fluid flows to the dryer 41.

A representative fermentation process to produce yeast cells is conducted in an aqueous biosynthetic system comprising methanol as the source of carbon and energy, yeast call inoculum (*Hansenula polymorpha*), an aqueous growth medium, and a source of oxygen. The growth medium comprises water, suitable minerals, growth factors biotin and thiamine, and a nitrogen source assimilable by the yeast. The pH of the fermentation vessel contents is controlled at 5.0 and the temperature employed for the fermentation is 40° C. After a suitable period of time, the fermentation reaction mixture contains a yeast cell concentration of 20 grams per liter.

Product from the fermenter can be centrifuged to provide a yeast slurry or paste. In the practice of a preferred embodiment of the heating method of this invention, the yeast slurry or paste can be conducted to a reactor having therein normal hexane. The yeast slurry and normal hexane can be heated at 150° C and vigorously agitated under autogenous pressure for 10 minutes. Heating can be terminated and the pressure rapidly reduced by venting to atmospheric pressure. Yeast can be removed from the vessel and allowed to cool at ambient temperature in a moving current of air to give a yeast product having less than 13 percent water by weight.

It is to be understood that while we have illustrated and described certain forms of our invention, it is not to be limited to the specific arrangement of steps of the process or parts of the apparatus as described and illustrated above.

What is claimed and desired to be secured by letters patent is:

1. A process for reducing the water content of a dispersion of microorganisms in an aqueous medium, said process comprising the steps of:
   a. contacting a dispersion of microbial cells in an aqueous medium with a heating medium containing at least one hydrocarbon selected from a group comprising $C_3$–$C_8$ hydrocarbons at a temperature at least about 100° C for a time sufficient to dewater said cells to a water content of less than about 13 percent by weight; and
   b. separating the heating medium from the microbial cells.

2. The process as set forth in claim 1 wherein said temperature is between about 100° C and 250° C.

3. The process as set forth in claim 1 wherein said temperature is between about 150° C and 175° C.

4. The process as set forth in claim 1 wherein said hydrocarbon is selected from a group comprising $C_3$–$C_8$ alkanes.

5. The process as set forth in claim 4 wherein the selected said alkane is hexane.

6. The process as set forth in claim 1 wherein the hydrocarbon is maintained at a pressure sufficient to maintain said hydrocarbon in a liquid state.

7. The process as set forth in claim 1 wherein said hydrocarbon is maintained at a pressure sufficient to maintain said hydrocarbon in a gaseous state.

8. The process as set forth in claim 1 wherein said separated heating medium is recovered and recycled for contacting the microbial cells.

* * * * *